United States Patent
Guidotti et al.

[11] Patent Number: 6,037,518
[45] Date of Patent: *Mar. 14, 2000

[54] ABSORBENT BODY IN AN ABSORBENT PRODUCT

[75] Inventors: Ted Guidotti, Gothenburg; Christina Steger, Mölndal; Urban Widlund, Mölnlycke; Eje Österdahl, Västra Frölunda, all of Sweden

[73] Assignee: SCA Hygiene Products AB, Goteborg, Sweden

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/640,778
[22] PCT Filed: Dec. 27, 1994
[86] PCT No.: PCT/SE94/01259
§ 371 Date: May 21, 1996
§ 102(e) Date: May 21, 1996
[87] PCT Pub. No.: WO95/17870
PCT Pub. Date: Jul. 6, 1995

[30] Foreign Application Priority Data

Dec. 29, 1993 [SE] Sweden .................................. 9304321

[51] Int. Cl.⁷ ....................................................... A61F 13/15
[52] U.S. Cl. ...................... 604/378; 604/385.1; 604/379; 604/380
[58] Field of Search ..................................... 604/378, 379, 604/380, 385.1, 384

[56] References Cited

U.S. PATENT DOCUMENTS

| | | |
|---|---|---|
| 3,897,784 | 8/1975 | Fitzgerald . |
| 4,184,498 | 1/1980 | Franco ..................................... 604/375 |
| 4,333,462 | 6/1982 | Holtman et al. . |
| 4,333,463 | 6/1982 | Holtman et al. . |
| 4,397,644 | 8/1983 | Matthews et al. . |
| 4,413,996 | 11/1983 | Taylor . |
| 4,501,586 | 2/1985 | Holtman et al. . |
| 4,531,945 | 7/1985 | Allison ..................................... 604/378 |
| 4,973,325 | 11/1990 | Sherrod et al. . |
| 4,988,344 | 1/1991 | Reising et al. . |
| 4,994,037 | 2/1991 | Bernardin . |
| 5,134,007 | 7/1992 | Reising et al. . |

FOREIGN PATENT DOCUMENTS

| | | |
|---|---|---|
| 20518/76 | 6/1978 | Australia . |
| 0 254 476 | 1/1988 | European Pat. Off. . |

(List continued on next page.)

Primary Examiner—John G. Weiss
Assistant Examiner—Dennis Ruhl
Attorney, Agent, or Firm—Burns, Doane, Swecker & Mathis, L.L.P.

[57] ABSTRACT

Absorbent body in an absorbent product such as a diaper, incontinence pad, sanitary napkin or the like, and which comprises a liquid acquisition portion (13; 11, 13) and a liquid storage portion (12) adjacent thereto. The liquid acquisition portion has at least one well (13) which is located at the assumed wetting area of the absorbent body and extends into and through the liquid storage portion (12) and is in liquid communication with a liquid wicking layer (14) arranged under the liquid storage layer (12). The material in the liquid acquisition portion (13; 11, 13) has a mean pore size which is greater than the mean pore size in the liquid storage portion (12). The absorbent body has a high instantaneous absorption even during repeated wetting and a low rewetting.

27 Claims, 4 Drawing Sheets

FOREIGN PATENT DOCUMENTS

| | | |
|---|---|---|
| 0 316 771 | 5/1989 | European Pat. Off. . |
| 0 354 196 | 2/1990 | European Pat. Off. . |
| 0 470 392 | 2/1992 | European Pat. Off. . |
| 0 536 941 | 4/1993 | European Pat. Off. . |
| 2 082 643 | 3/1982 | United Kingdom . |
| 2 124 907 | 2/1984 | United Kingdom . |
| WO 90/05808 | 5/1990 | WIPO . |
| WO 92/11830 | 7/1992 | WIPO . |
| 93/15702 | 8/1993 | WIPO . |
| WO 93/15702 | 8/1993 | WIPO . |

ABSORBENT BODY IN AN ABSORBENT PRODUCT

TECHNICAL AREA

The present invention relates to an absorbent body in an absorbent product, such as a diaper, incontinence pad, sanitary napkin or the like and comprises a fluid acquisition portion and a fluid storage portion adjacent thereto.

THE BACKGROUND OF THE INVENTION

An absorbent body for absorbent products such as disposable diapers, incontinence protectors and sanitary napkins is usually constructed of one or more layers of hydrophilic fibres, e.g. cellulose fluff. Furthermore, so-called superabsorbents are often included, which are polymers with the capacity to absorb many times their own weight in water or bodily fluid. Furthermore, additional components can sometimes be included in the absorbent body in order to improve, for example, its fluid spreading properties or to increase its coherence and ability to resist deformation during use.

A major problem, primarily in adult diapers and incontinence protectors intended to receive and absorb relatively large quantities of fluid, is that they often leak before their total absorbent capacity is completely used up. Since during urination, large quantities of fluid are often expelled during a few seconds, it is not uncommon that this results in the absorbent body being temporarily locally saturated with urine in the so-called fluid acquisition zone, when there is not enough time for the urine to be spread out to the other portions of the absorbent body and thus any more urine expelled will leak out of the diaper. Such early leakage is, of course, a great source of irritation for both the user and his caretaker. The leakage problem is accentuated upon repeated wetting.

Another problem is keeping the surface facing the user as dry as possible during the entire use and preventing so-called re-wetting, i.e. that already absorbed fluid is pressed back out of the absorbent body and wets the skin of the user or gives rise to leakage. To a certain extent, this re-wetting problems are alleviated if the absorbent body contains superabsorbents, which chemically bond the absorbed fluid even when the product has been subjected to external pressure, for example when the user sits down. One difficulty is, however, to design the absorbent body in such a way that the fluid is spread from the wetting area to unused portions of the absorbent body.

International patent application WO-A-9315702 describes an absorbent body comprising at least two different cellulose fluffs, the fibre structure in the first absorbent layer substantially consisting of a first type of fluff with an open fibre structure and low liquid dispersability, for example a cellulose fluff made chemo-thermal mechanically, and a fibre structure in the other absorbent layer essentially consisting of a second type of fluff with higher liquid dispersability than the fluff in the first absorbent layer, for example a chemically produced fluff. The first layer can, by virtue of its open fibre structure, house much liquid between the fibres and therefore can receive large amounts of liquid during a short period of time, i.e. it has a high momentaneous liquid absorbtion capacity. The other layer, which has a higher liquid dispersability than the first layer, is able to drain liquid from the first layer and spread it to the other layer.

EP-A-0,254,476 discloses an absorbent body, which in one zone essentially in front of the wetting area, has a lower surface weight and a lower density than the surrounding portions of the absorbent body. This provides an area with high momentaneous liquid absorption capacity, whereafter the liquid can be dispersed and stored in the surrounding areas of the absorbent body.

GB-A-2,082,643 describes an absorbent body with an essential uniform surface weight but with a density gradient in the longitudinal direction, so that the density increases towards the short sides of the absorbent body. This provides rapid liquid admittance in the central portion of the absorbent body out towards the more compressed end portions.

U.S. Pat. No. 4,413,996 describes an absorbent body for a diaper having a liquid absorbing depression or well in the wetting area. In this well, a porous batt can possibly be arranged.

There is, however, still room for improvement as regards liquid absorption capacity and dispersability, especially in products intended to be able to receive large quantities of liquid during a short period of time, which is often the case in, for example, incontintence products for adults. Another goal is that the surface of the absorbent body facing the user must be felt to be dry and comfortable, even after repeated wetting.

THE PURPOSE AND ESSENTIAL FEATURES OF THE INVENTION

The purpose of the present invention is to provide an absorbent body of the type described by way of introduction, which fulfills the goals, i.e. which can rapidly receive large quantities of liquid even upon repeated wetting, and disperse the liquid by wicking towards the unused portions of the absorbent body, and which also has a high surface dryness. This has been achieved by virtue of the fact that said liquid acquisition portion comprises at least one well located at the assumed wetting area of the absorbent body and extending depthwise into and through the liquid storage portion and is in liquid communication with a wicking layer arranged under the liquid storage layer, and in that in the liquid storage portion there is arranged a first absorbent structure which has a first effective mean pore size and that in the liquid acquisition portion including the well(s) there is arranged one or more second absorbent structures, each having an effective mean pore size, which is larger than the first mean pore size.

DESCRIPTION OF EXAMPLE

Figure 1:
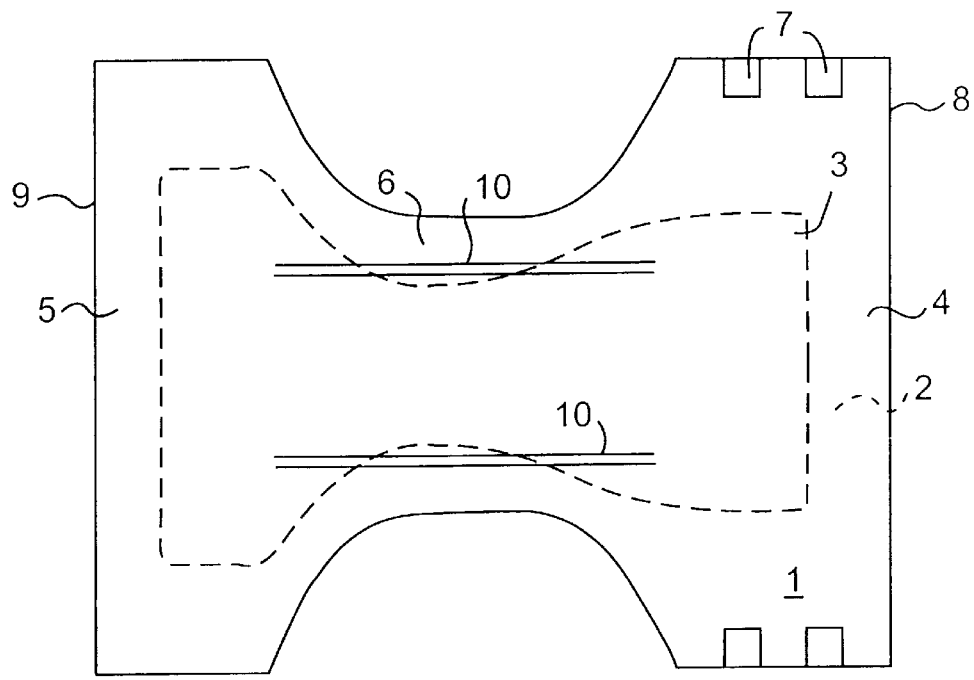
FIG. 1 shows a plan view of a diaper as seen from the side facing the user.

The diaper shown in FIG. 1 comprises a liquid permeable cover layer 1, for example of fibre fabric or perforated plastic film, a liquid impermeable cover layer 2, for example of plastic film or hydrophobic fibre fabric, and an absorbent body 3 enclosed between the two cover layers 1 and 2.

The diaper is intended to enclose the lower portion of the user's torso as a pair of absorbent pants. It has a rear portion 4 intended to face the rear of the user, a front portion intended to face the front of the user, and a narrower crotch portion 6 between the back portion 4 and the front portion 5. In order to be able to join the diaper together to the desired pant shape, tape tabs 7 are arranged adjacent the rear waist edge 8 of the diaper. The tape tabs 7 are fixed when used against the exterior of the front portion 5 of the diaper, close to the front waist edge 9, thus holding the diaper together about the waist of the user. Other fastening means, such as Velcro®, hooks and the like are of course also conceivable.

Furthermore, the diaper according to FIG. 1 comprises pretensioned elastic means 10, which can consist of a suitable material, such as elastic foam, elastic tape or thread-wound elastic cords. For the sake of simplicity, the cords are shown in FIG. 1 in their extended state. As soon as the tension is released, the elastic means will contract and thereby form the elastic leg bands of the diaper.

It should be pointed out here that the diaper shown in the drawing and described above is in no way a limiting example. Thus, the shape of the diaper as well as its other design features can be varied. For example, for diapers intended to be worn inside a special pair of fixing pants, the fastening means, i.e. the tape tabs 7, can be eliminated as can possibly the elastic means 10 as well.

Figure 4:
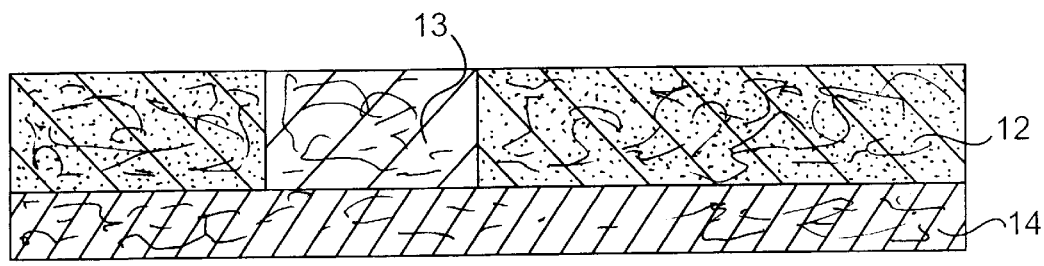
FIGS. 4 and 5 are corresponding sections but through alternative embodiments of the absorbent body.

With reference to the example shown in FIG. 4, the absorbent body 3 of the diaper is composed of a number of different parts. Essentially directly in front of the assumed wetting area of the diaper, which is the area of the diaper which is first struck by the emitted urine, and which is usually displaced somewhat towards the front portion of the diaper, the absorbent body 3 has a liquid acquisition well 13 which extends into and straight through a surrounding liquid storage layer 12. The well 13 can rapidly receive great amounts of liquid during a short period of time. Beneath the storage layer 12 and the well 13, there is a wicking layer 14 consisting of a fibre material with high liquid dispersability.

The fibre material in the well 13 can consist, for example, of cellulose fibres of mechanical pulp, thermo-mechanical pulp, or chemo-thermo-mechanical pulp, so-called CTMP. These pulps have relatively coarse fibres with remaining lignin, and therefore they have relatively large pore volume, high wet resilience and low liquid dispersability. High wet resilience means that the fluff pulp essentially retains its structure even after wetting. Other fluff pulps with similar properties can be used, for example southern pine or chemically stiffened cellulose fibres, as well as synthetic fibres.

Figure 3:
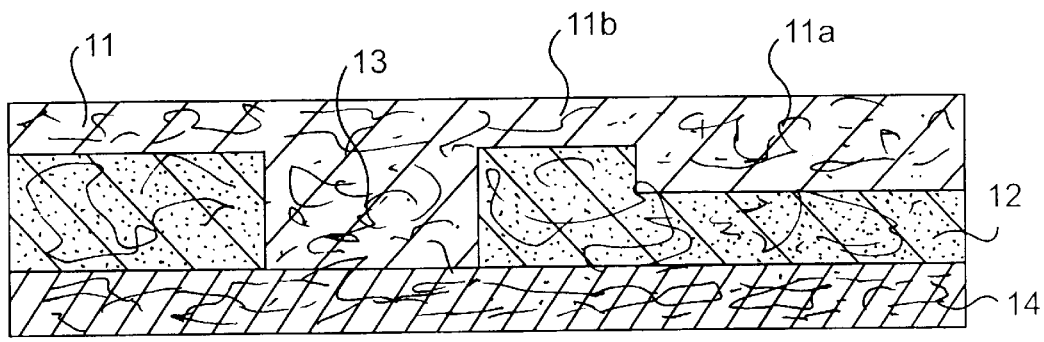
FIG. 3 is a section along the line III—III in FIG. 2.
Figure 5:
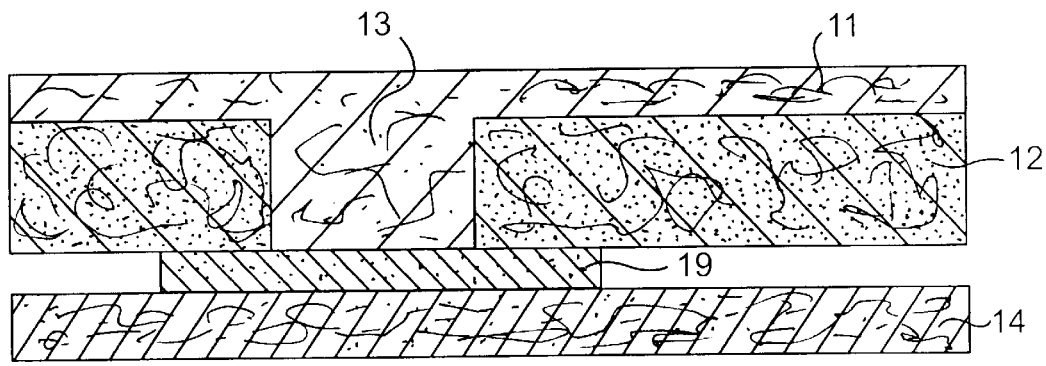

According to the example shown in FIGS. 3 and 5, there is arranged on top of the storage layer 12 a cover layer 11, which together with the well 13 forms the liquid acquisition portion of the absorbent body. The cover layer 11 and the well 13 can, as shown, be integrated with each other and thus consist of the same material. They can, however, also consist of different materials, both of which should, however, have the desired properties, such as relatively large pore size, high wet resilience and low liquid dispersability. The cover layer increases the surface dryness of the absorbent body.

The cover layer 11 has, in the embodiment shown in FIG. 3, a thicker rear portion 11a, as seen in the position of use of the absorbent body, said thicker portion changing, at a certain distance from the well 13, preferably 5–50 mm, to a thinner portion 11b. The thinner portion 11b has a higher density than the thicker portion 11a and therefore functions as a liquid barrier preventing liquid from being spread towards the rear portion 11a of the cover layer 11, which is thus kept dry. An additional advantage is that urine and faeces are kept separate from each other. Mixing of urine and faeces results in the formation of undesirable decomposition products, which can cause skin irritation. The well 13 can, of course, also be completely surrounded by such a barrier 11a of the cover layer 11. The higher density of the portion 11b is automatically obtained by compression of the absorbent body, thanks to the reversed thickness ratio of the underlying storage layer 11, presupposing that it has a higher resistance to compression than the cover layer 11. A compressed barrier strip 11b next to the well 13 can of course be achieved in other manners.

The example shown in FIG. 4 lacks the cover layer 11.

According to the example shown in FIG. 5, there is between the well 13 and the wicking layer 14 a liquid acquisition layer 19. This should consist of a material with a high liquid receptability and wet resiliance, i.e. it should retain an open fibre structure even in a wet state. Examples of suitable materials are synthetic fibre material, e.g. in the form of a wet, polymer form material, cellulose fibres of mechanical pulp, thermo-mechanical pulp, chemo-thermo-mechanical pulp (so-called CTMP) or chemically stiffened cellulose fibres. The layer 19 can also consist of a material which swells upon wetting, e.g. compressed dry formed sheet pulp.

The fibre material in the storage layer 12 should substantially consist of fluff pulp or other fibre material with relatively small pore volume and high liquid dispersability. Fluff pulps made chemically, which consist of fine fibres of essentially pure cellulose, have in general good liquid dispersability. Even fluff pulp of, for example, CTMP compressed to a density of over about 0.12 g/cm$^3$ has relatively good liquid dispersion properties.

Another material with good liquid dispersion properties is compressed dry-formed sheet pulp of for example CTMP or chemical pulp. Such materials are described in WO 90/0508.

The fibre material in the wicking layer 14 should consist substantially of chemical fluff pulp, dry-formed sheet pulp according to the above or other fibre material with good dispersion properties.

The density in the liquid acquisition portion 11, 13 should be between 0.02 and 0.2 g/cm$^3$, and preferably between 0.06 and 0.15 g/cm$^3$. The density in the storage layer 12 should be between 0.1 and 1.0 g/cm$^3$, preferably between 0.12 and 0.6 g/cm$^3$. The density in the wicking layer 14 should be 0.08–1.0 g/cm$^3$, and preferably 0.12–0.6 g/cm$^3$. The density values given above apply for absorbent bodies of cellulose fluff pulp. For other types of absorbent materials, other densities can be suitable.

The difference in pore size between the liquid acquisition portion 11, 13, on one hand, and the storage layer 12 and the wicking layer 14, on the other hand, can be achieved by a difference in density between the layers, but even at the same density, but with different types of fibre materials, the desired pore size difference can be achieved.

The liquid acquisition portion 11, 13 contains between 0 and 30%, preferably between 2 and 15% of superabsorbent, computed on the total dry weight of the portion. The superabsorbent, in the form of flakes, fibres, granules, powder or the like, is preferably mixed with the fibre material, either substantially evenly distributed or in such a manner that certain portions can contain a higher proportion of superabsorbent than others. Its purpose is to absorb and bind any liquid which remains in the liquid acquisition portion 11, 13, even after it has been drained by the storage layer 13 and the wicking layer 14. This provides a dry surface closest to the user, since the spaces between the fibres in the liquid acquisition portion 11, 13 are essentially emptied of liquid.

The superabsorbent in the liquid acquisition portion 11, 13 should have a high gel strength, so that an open fibre structure is retained in this portion even after wetting, and it is an advantage if it has a relatively low absorption rate. The liquid acquisition portion 11, 13 can of course be completely free of superabsorbents.

The storage layer, as well, preferably contains superabsorbent, between 2 and 80%, preferably between 10 and 50%, computed on the total dry weight of the layer. The superabsorbent in the form of flakes, fibres, granules, powder or the like is either mixed with the fibre material or applied in the form of one or more layers between the layers of fibres. The superabsorbent is either evenly distributed in the storage layer 12 or with varying concentration across the length and/or thickness of the absorbent body.

It is also conceivable to have as a storage layer 12 an essentially pure layer of superabsorbent.

The superabsorbent in the storage layer 12 has preferably a high absorption capacity under pressure, i.e. a capacity to swell essentially uneffected by normally occurring compressive forces, in order to not block or impede the dispersion of liquid. What characterizes these superabsorbents is a high degree of cross-linking, which makes them more difficult to press together in comparison with a gel with a lower degree of cross-linking.

The storage layer 12 can, of course, also be completely free of superabsorbent.

The wicking layer 14 is preferably free of or contains very small amounts of superabsorbent.

The exuded body liquid, in this case urine, can be rapidly absorbed by the liquid acquisition portion 11, 13, and be spread either directly or via the wicking layer 14 onto the second absorption layer 12, where it is stored. The difference in capillary size between the fibre materials in the liquid acquisition portion 11, 13 and the storage layer 12 creates a suction directly from the liquid acquisition portion 11, 13 towards the storage layer 12 or the wicking layer 14.

The liquid acquisition portion 11, 13 is drained of liquid and is prepared to receive the next dose of liquid. The storage layer 12 has a capacity for storing several doses of liquid.

Figure 2:
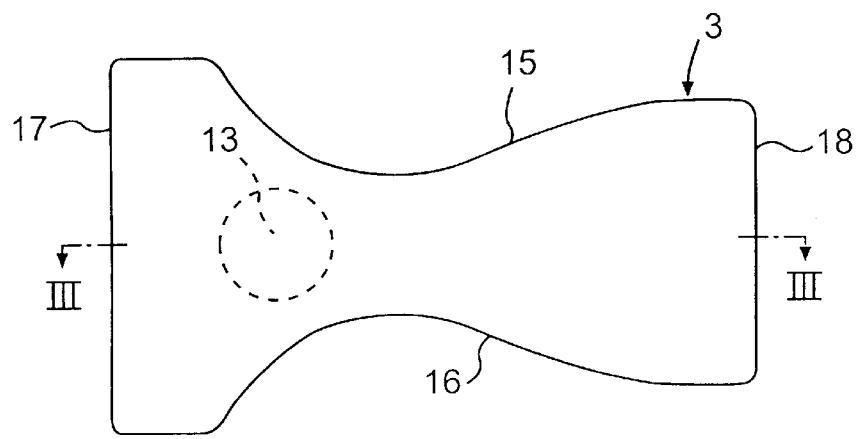
FIG. 2 shows a plan view of an absorbent body in the diaper according to FIG. 1.
Figure 6:
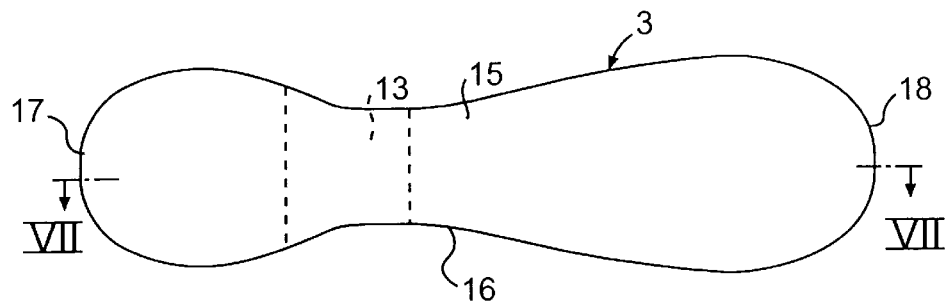
FIG. 6 shows a plan view of another absorbent body.
Figure 7:
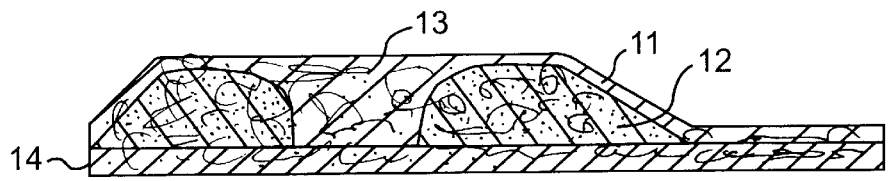
FIG. 7 is a section along the line VII—VII in FIG. 6.

The well 13 can have varying shape and size. It is important, however, that it has a portion which is located in the assumed wetting area of the absorbent body, i.e. is displaced toward the front portion thereof. The well 13 can extend transversely to the absorbent body out to the longitudinal lateral edges 15, 16, as is shown in FIG. 6, or terminate inside them, as is shown in FIG. 2. In both of the examples, the well 13 is located only in the front portion of the absorbent body and terminates slightly inside its front edge 17. It is, however, conceivable that the well 13 extends up to the front edge and that it even extend somewhat into the rear portion of the absorbent body, possibly to its rear edge 18.

Figure 8:
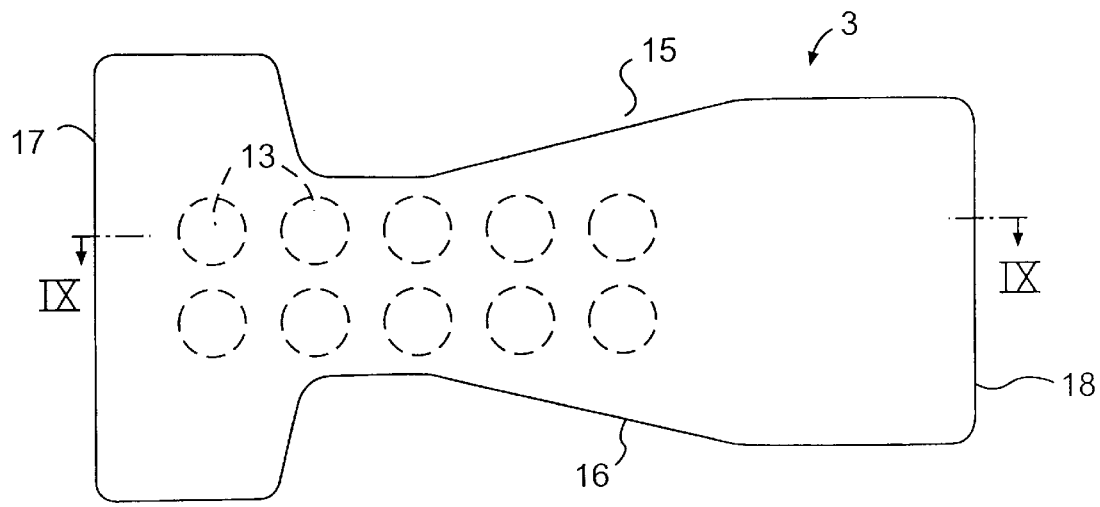
FIG. 8 shows a plan view of still another absorbent body.
Figure 9:
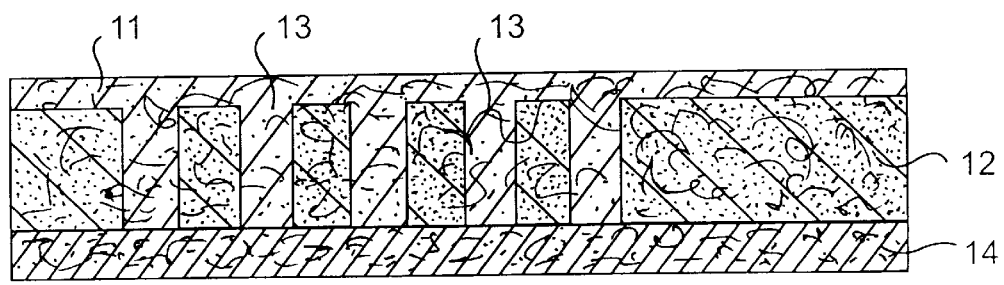
FIG. 9 is a section along the line IX—IX in FIG. 8.

According to an additional variant, the absorbent body has two or more wells. Such an embodiment is shown in FIGS. 8 and 9. An advantage of having several small wells 13 instead of one big well is that the wetting area of a diaper may vary depending on whether the user is lying or sitting and it also varies between males and females. With more than one well the risk that the urine will strike the absorbent body outside the well is reduced. A small well is also more rapidly drained from liquid than a big well, which is a further advantage. The wells may also have different sizes in different areas of the absorbent body.

The absorbent materials described above have only fibre based structures. It is, however, possible according to the invention, to use other types of porous absorbent materials, such as polymer foams, for example polyester, polyurethane, polyolefines, viscose, etc., or porous polymeric macro structures. The desired pore size difference between the liquid acquisition portion and the storage portion can be achieved simply with such materials as well. Even combinations of fibre and foam materials can be used.

By pore size is meant here the effective mean pore size which the structure has in dry state. A measuring method for determining and measuring the effective mean pore size in a fibre structure is described in EP-A-0,470,392. An alternative embodiment involves the use as a liquid acquisition portion, especially as a well 13, a hard compressed material, which expands when wetted. Repeated wettings will thus give it an expanded and increased pore volume. Examples of such materials are compressed dry formed sheet pulp, compressed structures of chemically stiffened cellulose fibres and compressed thermal bound fibre structures, where wetting breaks the thermal bonds and the structure is allowed to expand.

A few comparative tests are described below comparing an absorbent body according to the invention with an absorbent body without a well 13.

EXAMPLES

The instantaneous absorption and rewetting were tested for two fluff pulp bodies A and B 10×28 cm, each consisting of an upper layer of CTMP pulp of soft wood, a storage layer located thereunder of chemical pulp of soft wood and thereunder a dispersion layer of chemical pulp of soft wood. The upper layer of the sample body A contained 1.2 g of superabsorbent, essentially homogeneously mixed with the fluff pulp fibres, while the upper layer of the sample body B contained 0.8 g of the same superabsorbent, essentially homogeneously mixed. The weight per unit area of the upper layer in the sample body A was 400 g/m$^2$. The weight per unit area in the upper layer in the sample body B was 200 g/m$^2$. The sample body B had a well of the same material and density as the upper layer. The well had a cross-sectional area in the form of a circle with the diameter 9 cm. The mean density of the sample body B in the well area was 0.07 g/cm$^3$, while the mean density outside the well area was 0.11 g/cm$^3$.

The storage layer in the sample body A had a weight per unit area of 600 g/m$^2$ and a density of 0.125 g/cm$^3$. Immediately thereunder, i.e. between the storage layer and the wicking layer, there was supplied a layer of 4.5 g of superabsorbent. The weight per unit surface of the wicking layer was 300 g/m$^2$. The mean density of the sample body A was 0.2 g/cm$^3$.

The storage layer in the sample body B had a weight per unit area of 500 g/m$^2$, a density of 0.125 g/cm$^3$ and contained 4.6 g of the same superabsorbent as the sample body A, essentially homogeneously mixed into the fluff pulp. The wicking layer in the sample layer B had a weight per unit area of 250 g/m$^2$.

Instantaneous Absorption

Figure 10:
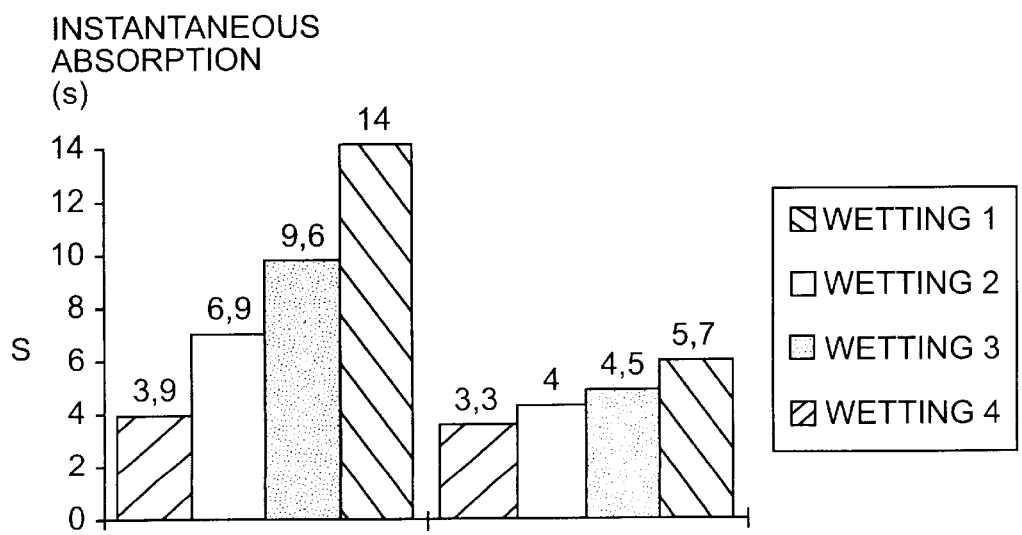
FIG. 10 shows in the form of a stack diagram the momentaneous absorption of an absorbent body (B) according to the invention and another absorbent body (A).

Four additions of each 60 ml of liquid (0,9% NaCl solution) were made at a certain time interval. The time it took until all the liquid was absorbed was measured (visual observation). The result is shown in FIG. 10 in the form of a bar graph. The sample body B had a substantially better instantaneous absorption than the sample body A, especially at the second, third and forth wetting. The sample body B retained its rapid instantaneous absorption during the repeated wettings.

Rewetting

The rewetting was measured just before the forth liquid addition by a filter paper being placed over the wetting point and being loaded with a weight of 1.1 kg (2.8 kPa) for 15 seconds. The filter papers were weighed before and after the loading and the rewetting was noted. The sample body A had a rewetting of 3.5 g and the sample body B had a rewetting of 2.3 g, i.e. there was a lower degree of rewetting for sample body B.

In conclusion, the tests show a significally improved instantaneous absorption, especially upon repeated wetting, for the sample body containing the liquid acquisition well according to the invention. Furthermore, it had a lower rewetting. Thus, the invention has achieved an absorbent body with very good absorption properties.

We claim:

1. Absorbent body for use in a diaper or an incontinence product, said absorbent body comprising:
   a liquid acquisition portion, a liquid storage portion adjacent thereto and a liquid wicking layer in fluid communication with the liquid acquisition portion,
   wherein said liquid acquisition portion comprises at least one well located at an expected wetting area of the absorbent body for receiving a large amount of liquid during a short period of time, said well extending depthwise into and through the liquid storage portion and is in liquid communication with the liquid wicking layer arranged under the liquid storage layer,
   wherein in the liquid storage portion there is arranged a first absorbent structure which has a first effective mean pore size and in the liquid acquisition portion including the well(s) there is arranged one or more second absorbent structures, each of said one or more second absorbent structures having an effective mean pore size, which is larger than the first mean pore size of said first absorbent structure, said liquid storage portion promoting communication of fluid contained in said liquid acquisition portion into said liquid storage portion such that said liquid acquisition portion may receive a further amount of liquid,
   said liquid wicking layer being defined by a mean pore size different from said effective mean pore size of the one or more second absorbent structures of the liquid acquisition portion, the difference in effective mean pore size causing liquid to be drawn from said at least one well to said wicking layer in fluid communication therewith, said wicking layer dispersing liquid away from said at least one well and throughout said wicking layer in order to increase an effectiveness of the storage portion in absorbing liquid therefrom and thereby assisting said liquid acquisition portion in receiving the further amount of liquid.

2. Absorbent body according to claim 1, wherein the first and/or the second absorbent structures comprise hydrophilic fibre material.

3. Absorbent body according to claim 1, wherein the first and/or the second absorbent structures comprise polymer foam material.

4. Absorbent body according to claim 1, wherein the liquid acquisition portion has a lower density than the liquid storage portion.

5. Absorbent body according to claim 1, wherein the liquid acquisition portion has a density of 0.02–0.2 g/cm$^3$, and the liquid storage portion has a density of 0.1–1.0 g/cm$^3$.

6. Absorbent body according to claim 2, wherein the fibre material in the liquid acquisition portion has an open fibre structure and a low liquid dispersability, and that the fibre materal in the liquid storage portion has a higher liquid dispersability than the fibre material in the liquid acquisition portion.

7. Absorbent body according to claim 6, wherein a major portion of the fibre material in the liquid acquisition portion is mechanical pulp, thermo-mechanical pulp, chemi-thermomechanical pulp, pulp of chemically stiffened cellulose fibres, synthetic fibres or mixtures thereof.

8. Absorbent body according to claim 4, wherein a major portion of the fibre material in the liquid storage portion is chemical pulp.

9. Absorbent body according to claim 4, wherein a major portion of the fibre material in the liquid storage portion is dry formed sheet pulp.

10. Absorbent body according to claim 1, wherein the liquid acquisition portion contains between 0 and 30% of superabsorbent material computed on the total dry weight of the liquid acquisition portion.

11. Absorbent body according to claim 1, wherein the liquid storage portion contains between 2 and 80% of superabsorbent material computed on the total dry weight of the liquid storage portion.

12. Absorbent body according to claim 1, wherein the liquid storage portion consists of a layer of superabsorbent material in particle form.

13. Absorbent body according to claim 1, wherein said at least one well comprises two or more wells distributed over the assumed wetting area of the absorbent body.

14. Absorbent body according to claim 1, wherein the liquid acquisition portion comprises a cover layer which covers at least substantial portions of the liquid storage portion.

15. Absorbent body according to claim 14, wherein the cover layer of the liquid acquisition portion and the well are integrated with each other and consist of the same type of material.

16. Absorbent body according to claim 14, wherein the cover layer of the liquid acquisition portion and the well consist of different types of material.

17. Absorbent body according to claim 15, wherein the cover layer has a compressed portion adjacent to the well, said compressed portion having a higher density than adjacent portions of the cover layer.

18. Absorbent body according to claim 17, wherein the cover layer in a rear portion of the absorbent body has a lower density than said compressed portion and that said rear portion is separated from the well by means of a margin of said compressed portion.

19. Absorbent body according to claim 18, wherein said margin has a dimension in the longitudinal direction of the absorbent body of between 5 and 50 mm.

20. Absorbent body according to claim 1, wherein between the well and the storage layer, there is arranged a layer of a material with high liquid absorption capacity and wetting resilience.

21. Absorbent product such as a diaper, incontinence protector, sanitary napkin or the like, and comprising an absorbent body according to claim 1 enclosed between a liquid permeable cover layer and a liquid impermeable cover layer.

22. Absorbent body according to claim 5, wherein the liquid acquisition portion has a density of between 0.06–0.15 g/cm$^3$.

23. Absorbent body according to claim 5, wherein the liquid storage portion has a density of between 0.12–0.6 g/cm$^3$.

24. Absorbent body according to claim 10, wherein the liquid acquisition portion contains between 2 and 15% of superabsorbent material computed on the total dry weight of the liquid acquisition portion.

25. Absorbent body according to claim 11, wherein the liquid storage portion contains between 10 and 50% of superabsorbent material computed on the total dry weight of the liquid storage portion.

26. Absorbent body according to claim 1, wherein between the well and the storage layer, there is arranged a layer of a material with high liquid absorption capacity and a capacity to swell in a wet state.

27. Absorbent body according to claim 1, wherein the mean pore size of said wicking layer is smaller than said effective mean pore size of the one or more second absorbent structures of the liquid acquisition portion such that capillary action causes fluid to be drawn from said larger effective mean pore size of said one or more second absorbent structures to the smaller mean pore size of said wicking layer.

* * * * *